United States Patent [19]

Doehner et al.

[11] Patent Number: 5,359,090

[45] Date of Patent: Oct. 25, 1994

[54] ALKOXYMETHYLATION OF PYRROLES

[75] Inventors: Robert F. Doehner, E. Windsor, N.J.; Jerry M. Barton, Langhorne, Pa.

[73] Assignee: American Cyanamid Company, Wayne, N.J.

[21] Appl. No.: 174,999

[22] Filed: Dec. 29, 1993

[51] Int. Cl.$^5$ .................. C07D 207/34; C07D 207/42
[52] U.S. Cl. .................... 548/561; 548/541; 548/543; 548/544; 548/546; 548/547; 548/548; 548/557; 548/558; 548/560; 548/562
[58] Field of Search ............... 548/541, 543, 544, 546, 548/547, 548, 557, 558, 560, 561, 562

[56] References Cited

U.S. PATENT DOCUMENTS

| | | | |
|---|---|---|---|
| 4,500,738 | 2/1985 | Schouten | 568/433 |
| 5,010,098 | 4/1991 | Brown et al. | 514/426 |
| 5,151,536 | 9/1992 | Kameswaran et al. | 548/530 |

OTHER PUBLICATIONS

CA 111: 115023n Pyrrole . . . Containing them, Dixon et al., p. 648, 1989.
CA 118: Preparation . . . Pesticides, Uhr et al., p. 813, 1993.
J. Muchowski and D. R. Solas, Journal of Organic Chemistry, 1984, pp. 203–205.

*Primary Examiner*—Johann Richter
*Assistant Examiner*—Joseph K. McKane
*Attorney, Agent, or Firm*—John W. Hogan, Jr

[57] ABSTRACT

There is provided a safe and effective means of introducing an alkoxymethyl group onto the ring Nitrogen atom of a wide variety of pyrrole compounds via the reaction of the appropriate pyrrole precursor sequentially with dialkoxymethane, Vilsmeier reagent and a tertiary amine. The product 1-(alkoxymethyl)pyrroles are useful as insecticidal, acaricidal, nematocidal and molluscicidal agents.

10 Claims, No Drawings

ALKOXYMETHYLATION OF PYRROLES

BACKGROUND OF THE INVENTION

Pyrrole carbonitrile, nitropyrrole, arylpyrrole, bisarylpyrrole, thioalkylpyrrole, alkylsulfonyl pyrrole, alkylsulfinylpyrrole thiocarboxamide pyrrole and heteroarylpyrrole compounds and derivatives thereof are highly effective insecticidal, acaricidal, nematocidal, molluscicidal and endecticidal agents useful in both plant and animal science. In general, the above-mentioned pyrrole derivatives having an alkoxymethyl substituent on the pyrrole ring Nitrogen atom are more efficacious than the parent pyrrole compounds.

The alkoxymethylation of pyrroles on Nitrogen to form N-(alkoxymethyl)pyrrole is generally achieved by the condensation of the appropriate pyrrole with an α-halomethyl ether in the presence of a strong base such as sodium hydride [i.e. J. Muchowski, et al, Journal of Organic Chemistry, 49 (1), p. 203 (1984)] or potassium t-butoxide (i.e. U.S. Pat. No. 5,010,098). However, the use of α-halomethyl ethers is not desirable in commercial or pilot plant scale production due to the severe carcinogenic properties of said ethers. Further, large scale employment of strong bases such as metal hydrides or t-butoxides is costly and hazardous.

The use of an alkylal and Vilsmeier reagent is known to give an alkoxymethyl ether of a phenolic hydroxyl group such as the process described in U.S. Pat. No. 4,500,738. However, this process is unsuccessful when applied to a pyrrole ring Nitrogen atom and no reaction takes place.

Therefore, it is an object of this invention to provide a safe and effective method for the preparation of N-(alkoxymethyl)pyrroles without the separate preparation of and handling of α-halomethyl ethers.

It is another object of this invention to provide a method for the alkoxymethylation of pyrroles without the use of strong bases such as metal hydrides or metal t-butoxides.

It is a further object of this invention to provide a readily available source of the N-alkoxymethyl derivatives of a wide variety of important pesticidal pyrrole compounds. Still further objects and features of the invention will become apparent from the description set forth below.

SUMMARY OF THE INVENTION

There is provided a safe and effective method for the preparation of a 1-(alkoxymethyl)pyrrole compound which comprises reacting a 1-H-pyrrole compound with di-(alkoxy)methane, dimethylformamide and phosphorous oxychloride in the presence of an aprotic solvent to form a reaction mixture and treating the reaction mixture with a tertiary amine, optionally at an elevated temperature.

A wide variety of pesticidal 1-(alkoxymethyl)pyrrole compounds may be prepared in high yield, efficiently and with greatly reduced environmental and human risk by the method of this invention such as pyrrole carbonitriles, nitropyrroles, arylpyrroles, bisarylpyrroles, thioalkylpyrroles, alkylsulfonylpyrroles, alkylsulfinylpyrroles, carboxamide pyrroles, thiocarboxamide pyrroles, heteroarylpyrroles and the like.

DETAILED DESCRIPTION OF THE PREFERRED EMBODIMENTS

Pyrrole compounds demonstrate many useful biological properties such as bacteriacidal, fungicidal, acaricidal, insecticidal, molluscicidal and nematocidal properties. A safe and effective method to derivatize the pyrrole ring Nitrogen would greatly advance both the medical and agricultural applications of the pyrrole art. In particular, the alkoxymethylation of pyrroles which demonstrate agricultural pesticidal properties, tends to lead to an enhancement of these properties. However, methods heretofore known in the art to alkoxymethylate the pyrrole ring Nitrogen incur the use and handling of either an α-halomethyl ether (carcinogenic) or a strong base such as a metal hydride or metal alkoxide (hazardous and costly) or both.

It has now been found that 1-H-pyrrole compounds may be alkoxymethylated on the pyrrole ring Nitrogen to give the 1-(alkoxymethyl)pyrrole product in good yield, and in the absence of strong metal bases, and without the need to isolate or handle carcinogenic intermediates, by the reaction of the 1-H-pyrrole compound with di($C_1$–$C_6$alkoxy)methane and Vilsmeier reagent in the presence of an aprotic solvent to form a reaction mixture and the subsequent addition of a tertiary amine to the reaction mixture to form the desired 1-($C_1$–$C_6$alkoxymethyl)pyrrole compound.

Surprisingly, the sequential addition of a tertiary amine to a mixture of a 1-H-pyrrole compound, di-($C_1$–$C_6$alkoxy)methane and Vilsmeier reagent in an aprotic solvent gives excellent conversion of the 1-H-pyrrole compound to the corresponding 1-($C_1$–$C_6$alkoxymethyl)pyrrole product.

In one embodiment of the invention a pyrrole compound of formula I

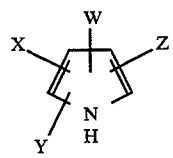

wherein
W is CN, $NO_2$, $S(O)_n CR$ or

X is hydrogen, halogen, CN, $NO_2$, $S(O)_m CR_3$, $C_1$–$C_4$haloalkyl, Q, or phenyl optionally substituted with one or more halogen, $NO_2$, CN, $C_1$–$C_4$alkyl, $C_1$–$C_4$haloalkyl, $C_1$–$C_4$alkoxy, or $C_1$–$C_4$haloalkoxy groups;
Y is hydrogen, halogen, $C_1$–$C_4$haloalkyl, or phenyl optionally substituted with one or more halogen, $NO_2$, CN, $C_1$–$C_4$alkyl, $C_1$–$C_4$haloalkyl, $C_1$–$C_4$alkoxy or $C_1$–$C_4$haloalkoxy groups;
Z is hydrogen, halogen or $C_1$–$C_4$haloalkyl;
n and m are each independently an integer of 0, 1 or 2;
R and $R_3$ are each independently $C_1$–$C_6$haloalkyl;
$R_1$ and $R_2$ are each independently $C_1$–$C_4$alkyl, $C_1$–$C_4$haloalkyl or phenyl optionally substituted with one or more halogen, $NO_2$, CN, $C_1$–$C_4$alkyl, $C_1$–$C_4$haloalkyl, $C_1$–$C_4$alkoxy or $C_1$–$C_4$haloalkoxy groups;
Q is

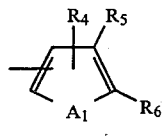

$R_4$, $R_5$ and $R_6$ are each independently hydrogen, halogen, $NO_2$, CHO or, $R_5$ and $R_6$ may be taken together with the atoms to which they are attached to form a ring in which $R_5R_6$ is represented by the structure:

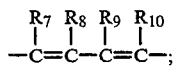

$R_7$, $R_8$, $R_9$ and $R_{10}$ are each independently hydrogen, halogen, CN or $NO_2$; and
A and $A_1$ are each independently O or S
may be safely and effectively converted to a 1-($C_1$-$C_6$alkoxymethyl)pyrrole compound of formula II

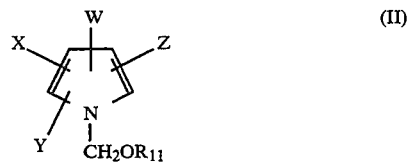

wherein W, X, Y and Z are as described above for formula I and $R_{11}$ is $C_1$-$C_6$alkyl.

In actual practice, a mixture of approximately stoichiometric amounts of a 1-H-pyrrole compound, di-($C_1$-$C_6$ alkoxy)methane, dimethylformamide and phosphorous oxychloride in an aprotic solvent is stirred at 0°-150° C., preferably 20°-60° C., for about 0.25-2.0 hours; the mixture is then treated with about 1-2 molar equivalents of a tertiary (3°) amine, stirred at 0°-150° C., preferably about 0°-60°, until the reaction is complete, and quenched with water to give the desired 1-($C_1$-$C_6$alkoxymethyl)pyrrole product. Using the 1-H-pyrrole compound of formula I as an example, the reaction is shown in flow diagram I wherein DMF is dimethylformamide and $R_{11}$ is $C_1$-$C_6$alkyl.

Flow Diagram I

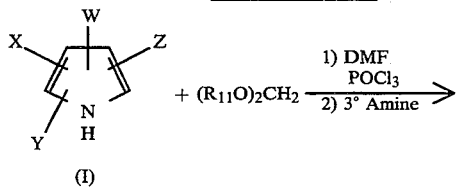

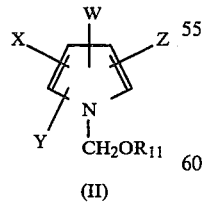

Although stoichiometric amounts of 1-H-pyrrole, di($C_1$-$C_6$alkoxy)methane, dimethylformamide and phosphorous oxychloride are suitable, a slight excess of Vilsmeier reagent (DMF and $POCl_3$), about 1.0-1.5 molar equivalents, is preferred and about 1.0-2.0 molar equivalents of di-($C_1$-$C_6$alkoxy)methane is preferred.

The stoichiometric measurements are based upon the molar equivalents of the starting 1-H-pyrrole compound used.

Aprotic solvents suitable for use in the method of invention are aromatic hydrocarbons, halogenated aromatic hydrocarbons, aliphatic nitriles, ethers and the like. Among the preferred aprotic solvents are toluene, xylenes, halobenzenes, and acetonitrile.

Reaction rate increases with increased temperature, however excessively high temperatures are disadvantageous and lead to side reactions and lowered yields. Temperatures suitable for the inventive process are those within a range of about 0°-150° C., preferably about 20°-60° C.

Tertiary amines suitable for use in the method of invention include any trisubstituted amine known in the art such as trialkylamine, dialkylarylamine, triarylamine, and the like, preferably trialkylamine, more preferably triethylamine.

It is contemplated that the method of invention be used to prepare the 1-(alkoxymethyl)derivative of a 1-H-pyrrole compound. Preferred 1-H-pyrrole compounds are compounds of formula I wherein W, X, Y and Z are as defined above. More preferred formula I compounds are those wherein W is CN or $NO_2$; X is hydrogen, halogen or $C_1$-$C_4$haloalkyl; Y is hydrogen, halogen, or $C_1$-$C_4$haloalkyl; and Z is halogen, $C_1$-$C_4$ haloalkyl or phenyl optionally substituted with one or more halogen or $C_1$-$C_4$ haloalkyl groups.

Preferred products of formula II obtained by the method of invention are those wherein $R_{11}$ is $C_1$-$C_6$alkyl; W is CN or $NO_2$; X is halogen or $C_1$-$C_4$haloalkyl; Y is halogen or $C_1$-$C_4$haloalkyl; and Z is phenyl optionally substituted with one or more halogen or $C_1$-$C_4$ haloalkyl groups. More preferred formula II products are those wherein $R_{11}$ is $C_1$-$C_3$alkyl (especially $C_2H_5$); W is CN; X is halogen; Y is $CF_3$; and z is phenyl optionally substituted with one chlorine or bromine atom.

In order to present a more clear understanding of the invention, the following examples are set forth below. These examples are merely illustrative, and are not to be understood as limiting the scope and underlying principles of the invention in any way.

The terms HPLC and $^1$HNMR designate high performance liquid chromatography and proton nuclear magnetic resonance, respectively.

EXAMPLE 1

Preparation of 4-Bromo-2-(p-chlorophenyl)-1-(ethoxymethyl)-5-(trifluoromethyl)-pyrrole-3-carbonitrile

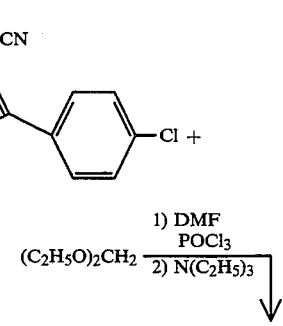

-continued

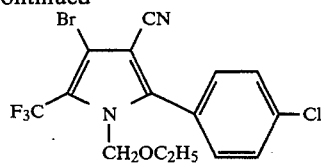

A stirred mixture of 4-bromo-2-(p-chlorophenyl)-5-(trifluoromethyl)pyrrole-3-carbonitrile (17.4 g, 0.05 mole), diethoxymethane (10.4 g, 0.10 mole) and dimethylformamide (DMF) (4.6 g, 0.0625 mole) in toluene, under $N_2$, is treated portion-wise with phosphorous oxychloride (9.6 g, 0.0625 mole) at 35°–45° C. over a 10 minute period, heated at 45°–53° C. for about 0.5 hour, cooled to 35° C. and treated dropwise with triethylamine (7.25 g, 0.0715 mole) over a 2 hour period at 35°–45° C. The reaction mixture is treated with water and the toluene is removed via azeotropic distillation. The remaining residue is treated with water, filtered and the filtercake is dried in vacuo at 60° C. to give the title product, 20.8 g, 92.7% pure, 94.6% yield, identified by HPLC analysis.

Using essentially the same procedure and substituting the following solvents for toluene, the title product is obtained in the yields shown below.

| Solvent | % Yield |
| --- | --- |
| Acetonitrile | 94.7 |
| Xylenes | 96.4 |
| Chlorobenzene | 93.6 |

EXAMPLE 2

Preparation of 4-Bromo-1-(n-butoxymethyl)-2-(p-chlorophenyl)-5-(trifluoromethyl)pyrrole-3-carbonitrile

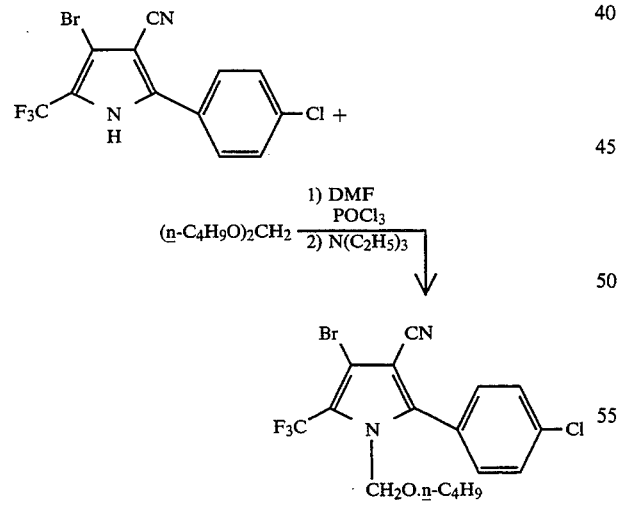

A stirred mixture of 4-bromo-2-(p-chlorophenyl)-5-(trifluoromethyl)pyrrole-3-carbonitrile (17.4 g, 0.05 mole), di-(n-butoxy)methane (12.0 g, 0.075 mole and dimethylformamide (DMF) (4.6 g, 0.063 mole) in xylenes, under $N_2$, is treated with phosphorous oxychloride (9.6 g, 0.063 mole) portion-wise at 30°–37° C. over a 10 minute period, heated at 45°–50° C. for 0.75 hour, cooled to 35° C., treated dropwise with triethylamine (8.1 g, 0.08 mole) over a 0.25 hour period and heated at 45°–50° C. for an additional 0.75 hour. The reaction mixture is then cooled to 25° C., treated with water and additional xylenes and stirred for 0.5 hour. The phases are separated and the organic phase is concentrated in vacuo to give the title product as a light brown solid, mp 52.0°–53.5° C., 20.6 g, 94.6% yield identified by $H^1NMR$ and mass spectral analyses.

EXAMPLE 3

Preparation of 4-Bromo-2-(p-chlorophenyl)-1-(methoxymethyl)-5-(trifluoromethyl)pyrrole-3-carbonitrile

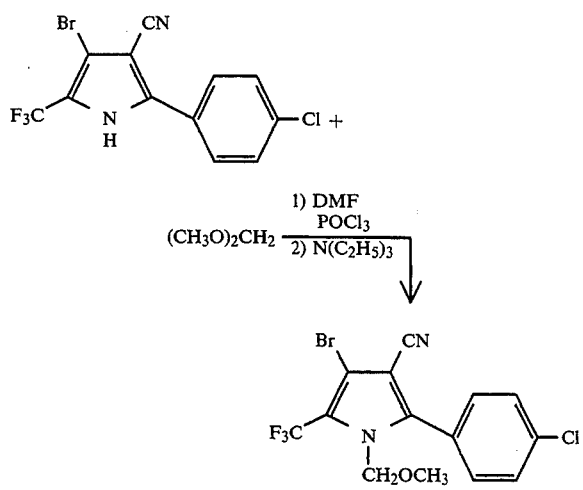

Using essentially the same procedure described in Example 2 and substituting dimethoxymethane for di(n-butoxy)methane, the title product is obtained in 66% yield, identified by $^1HNMR$ and mass spectral analyses.

EXAMPLE 4

Preparation of 2-(p-chlorophenyl)-1-(ethoxymethyl)-5-(trifluoromethyl)pyrrole-3-carbonitrile

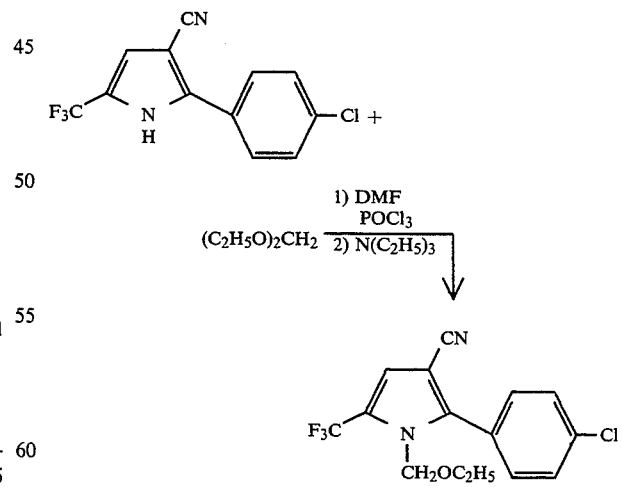

A stirred mixture of 2-(p-chlorophenyl)-5-(trifluoromethyl)pyrrole-3-carbonitrile (13.5 g, 0.05 mole), diethoxymethane (7.8 g, 0.075 mole) and dimethylformamide (5.5 g, 0.075 mole) in acetonitrile, under $N_2$, is treated with phosphorous oxychloride (11.5 g, 0.075 mole) over a 0.25 hour period at 39°–45° C., heated at 39°–45° C. for 0.75 hour and treated dropwise with triethylmine (10.1 g, 0.10 mole) at 45°–55° C. over a 0.5 hour period. The reaction mixture is diluted with water, stirred for 16 hours at 25° C. and concentrated in vacuo to give a crude product. The crude material is stirred at reflux temperature with a mixture of toluene and dilute aqueous NaOH and cooled to room temperature. The phases are separated and the organic phase is concentrated in vacuo to give the title product as a solid, mp 83°–84.5° C., 13.1 g, 80% yield, identified by mass spectral analysis.

What is claimed is:

1. A method for the preparation of a 1-(alkoxymethyl)pyrrole compound which comprises reacting a 1-H-pyrrole compound with di-(alkoxy)methane, dimethylformamide and phosphorous oxychloride in the presence of an aprotic solvent to form a reaction mixture and treating the reaction mixture with a tertiary amine, optionally at an elevated temperature.

2. The method according to claim 1 wherein the 1-H-pyrrole compound is a compound of formula I

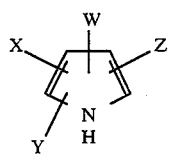

wherein

W is CN, $NO_2$, $S(O)_nCR$ or

X is hydrogen, halogen, CN, $NO_2$, $S(O)_mCR_3$, $C_1$–$C_4$haloalkyl, Q, or phenyl optionally substituted with one or more halogen, $NO_2$, CN, $C_1$–$C_4$alkyl, $C_1$–$C_4$ haloalkyl, $C_1$–$C_4$alkoxy or $C_1$–$C_4$ haloalkoxy groups;

Y is hydrogen, halogen, $C_1$–$C_4$haloalkyl, or phenyl optionally substituted with one or more halogen, $NO_2$, CN, $C_1$–$C_4$alkyl, $C_1$–$C_4$haloalkyl, $C_1$–$C_4$alkoxy or $C_1$–$C_4$haloalkoxy groups;

Z is hydrogen, halogen or $C_1$–$C_4$haloalkyl;

n and m are each independently an integer of 0, 1 or 2;

R and $R_3$ are each independently $C_1$–$C_6$haloalkyl;

$R_1$ and $R_2$ are each independently $C_1$–$C_4$alkyl, $C_1$–$C_4$ haloalkyl or phenyl optionally substituted with one or more halogen, $NO_2$, CN, $C_1$–$C_4$alkyl, $C_1$–$C_4$ haloalkyl, $C_1$–$C_4$alkoxy or $C_1$–$C_4$haloalkoxy groups;

Q is

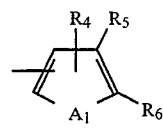

$R_4$, $R_5$ and $R_6$ are each independently hydrogen, halogen, $NO_2$, CHO or $R_5$ and $R_6$ may be taken together with the atoms to which they are attached to form a ring in which $R_5R_6$ is represented by the structure:

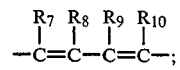

$R_7$, $R_8$, $R_9$ and $R_{10}$ are each independently hydrogen, halogen, CN or $NO_2$; and A and $A_1$ are each independently O or S.

3. The process according to claim 2 wherein
W is CN or $NO_2$;
X is halogen, $C_1$–$C_4$ haloalkyl or phenyl optionally substituted with one or more halogen or $C_1$–$C_4$ haloalkyl groups;
Y is hydrogen, halogen or $C_1$–$C_4$ haloalkyl; and
Z is hydrogen, halogen or $C_1$–$C_4$ haloalkyl.

4. The process according to claim 1 wherein the aprotic solvent is an aromatic hydrocarbon or an aliphatic nitrile.

5. The process according to claim 4 wherein the solvent is toluene, xylenes or acetonitrile.

6. The process according to claim 1 wherein the tertiary amine is tri($C_1$–$C_6$ alkyl)amine.

7. The process according to claim 6 wherein the amine is triethylamine.

8. The process according to claim 1 wherein the 1-(alkoxymethyl)pyrrole compound is a 1-($C_1$–$C_6$alkoxymethyl)pyrrole compound and the di-(alkoxy)methane is a di-($C_1$–$C_6$alkoxy)methane.

9. The process according to claim 8 wherein the di-($C_1$–$C_6$alkoxy)methane is di-(ethoxy)methane.

10. The process according to claim 9 wherein the 1-H-pyrrole compound has the structure

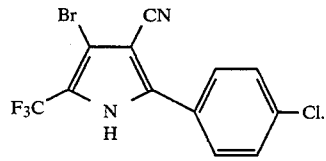

* * * * *